(12) United States Patent
High et al.

(10) Patent No.: US 10,614,503 B2
(45) Date of Patent: Apr. 7, 2020

(54) APPARATUS AND METHOD FOR SURVEYING PREMISES OF A CUSTOMER

(71) Applicant: Walmart Apollo, LLC, Bentonville, AR (US)

(72) Inventors: Donald R. High, Noel, MO (US); David C. Winkle, Bella Vista, AR (US); Michael D. Atchley, Springdale, AR (US)

(73) Assignee: Walmart Apollo, LLC, Bentonville, AR (US)

( * ) Notice: Subject to any disclaimer, the term of this patent is extended or adjusted under 35 U.S.C. 154(b) by 501 days.

(21) Appl. No.: 15/381,749

(22) Filed: Dec. 16, 2016

(65) Prior Publication Data

US 2017/0178222 A1 Jun. 22, 2017

Related U.S. Application Data

(60) Provisional application No. 62/269,820, filed on Dec. 18, 2015.

(51) Int. Cl.
*G06Q 30/00* (2012.01)
*G01C 11/00* (2006.01)
(Continued)

(52) U.S. Cl.
CPC ....... *G06Q 30/0631* (2013.01); *B64C 39/024* (2013.01); *B64D 47/08* (2013.01);
(Continued)

(58) Field of Classification Search
None
See application file for complete search history.

(56) References Cited

U.S. PATENT DOCUMENTS

| 8,929,178 B2 | 1/2015 | Lichter |
| 9,550,577 B1 | 1/2017 | Beckman |
(Continued)

FOREIGN PATENT DOCUMENTS

| CN | 103454556 A | 12/2013 |
| EP | 2884305 | 6/2015 |
(Continued)

OTHER PUBLICATIONS

A Towson remodeling company is using drones to survey roofs. Baltimore Business Journal. Sarah Gantz. Feb. 3, 2015. (Year: 2015).*

(Continued)

*Primary Examiner* — William J Allen
(74) *Attorney, Agent, or Firm* — Fitch, Even, Tabin & Flannery LLP (57) ABSTRACT

Systems, apparatuses and methods are provided herein for providing surveying premises of a customer. In one embodiment, a system for surveying premises of a customer comprises: an unmanned aerial vehicle (UAV) comprising a three dimension (3D) scanner and an image sensor, and a control circuit comprising a communication device configured to communicate with the UAV. The control circuit being configured to: receive, from a customer, a premises location, instruct the UAV to travel to the premises location to collect a set of data, form a 3D point cloud model of the premises based on 3D data collected by the 3D scanner of the UAV, identify one or more features of the premises based on the 3D point cloud model and image data collected by the image sensor of the UAV, and generate a recommendation to the customer based on the one or more features of the premises.

18 Claims, 4 Drawing Sheets

(51) Int. Cl.
*G06Q 30/06* (2012.01)
*B64D 47/08* (2006.01)
*B64C 39/02* (2006.01)
*G01B 11/25* (2006.01)

(52) U.S. Cl.
CPC .......... *G01B 11/2518* (2013.01); *G01C 11/00* (2013.01); *B64C 2201/123* (2013.01); *B64C 2201/127* (2013.01); *B64C 2201/146* (2013.01)

(56) References Cited

U.S. PATENT DOCUMENTS

| | | | |
|---|---|---|---|
| 9,573,684 | B2 | 2/2017 | Kimchi |
| 10,239,638 | B1 * | 3/2019 | Cohen ................. B64F 1/04 |
| 2009/0265193 | A1 | 10/2009 | Collins |
| 2012/0223965 | A1 * | 9/2012 | Pershing ............ G06F 17/5004 345/630 |
| 2014/0125651 | A1 | 5/2014 | Sharp |
| 2014/0254896 | A1 | 9/2014 | Zhou |
| 2014/0267627 | A1 * | 9/2014 | Freeman ............... G01S 17/023 348/47 |
| 2014/0312165 | A1 | 10/2014 | Mkrtchyan |
| 2014/0316614 | A1 | 10/2014 | Newman |
| 2015/0070188 | A1 * | 3/2015 | Aramburu ............ A01G 25/167 340/870.02 |
| 2015/0120094 | A1 | 4/2015 | Kimchi |
| 2015/0277440 | A1 | 10/2015 | Kimchi |
| 2016/0196755 | A1 | 7/2016 | Navot |
| 2016/0257401 | A1 | 9/2016 | Buchmueller |
| 2017/0110017 | A1 | 4/2017 | Kimchi |

FOREIGN PATENT DOCUMENTS

| | | |
|---|---|---|
| KR | 101519873 | 5/2015 |
| WO | 2015024694 | 2/2015 |

OTHER PUBLICATIONS

3DR; "Site Scan Features", https://3dr.com/enterprise/features/, printed Jun. 12, 2017, pp. 1-15.
PIX4D; "Real Estate", https://pix4d.com/industry/real-estate/, printed Jun. 12, 2017, pp. 1-3.
UKIPO; App. No. GB1621506.3; Combined Search and Examination Report under Sections 17 and 18(3) dated Jun. 15, 2017.
Antos, Matej; "The best 3D mapping software for UAV applications", Vespadrones, http://vespadrones.com/2015/11/29/the-best-3d-mapping-software-for-uav-applications/, Mar. 30, 2015, pp. 1-10.
Geomatics Technology Cluster; "Mapping and LIDAR", https://www.gtcluster.com/drupal/?q=en/node/28, printed Apr. 11, 2015, pp. 1-2.
UKIPO; App No. 1621506.3; Office Action dated Mar. 1, 2018.
UKIPO; App No. 1621506.3; Office Action dated Jul. 31, 2019.

* cited by examiner

APPARATUS AND METHOD FOR SURVEYING PREMISES OF A CUSTOMER

CROSS-REFERENCE TO RELATED APPLICATIONS

This application claims the benefit of U.S. Provisional Application No. 62/269,820, filed Dec. 18, 2015, which is incorporated herein by reference in its entirety.

TECHNICAL FIELD

This invention relates generally to unmanned aerial systems.

BACKGROUND

Conventionally, when a consumer shops for home improvement products, the consumer need to determine for themselves, the products that are suitable for their home's exiting items, layouts, and dimensions.

BRIEF DESCRIPTION OF THE DRAWINGS

Disclosed herein are embodiments of apparatuses and methods for surveying premises of a customer. This description includes drawings, wherein.

Elements in the figures are illustrated for simplicity and clarity and have not necessarily been drawn to scale. For example, the dimensions and/or relative positioning of some of the elements in the figures may be exaggerated relative to other elements to help to improve understanding of various embodiments of the present invention. Also, common but well-understood elements that are useful or necessary in a commercially feasible embodiment are often not depicted in order to facilitate a less obstructed view of these various embodiments of the present invention. Certain actions and/or steps may be described or depicted in a particular order of occurrence while those skilled in the art will understand that such specificity with respect to sequence is not actually required. The terms and expressions used herein have the ordinary technical meaning as is accorded to such terms and expressions by persons skilled in the technical field as set forth above except where different specific meanings have otherwise been set forth herein.

DETAILED DESCRIPTION

Generally speaking, pursuant to various embodiments, systems, apparatuses and methods are provided herein for surveying premises of a customer. A system for surveying premises of a customer comprises: an unmanned aerial vehicle (UAV) comprising a three dimension (3D) scanner and an image sensor, and a control circuit comprising a communication device configured to communicate with the UAV. The control circuit being configured to: receive, from a customer, a premises location, instruct the UAV to travel to the premises location to collect a set of data, form a 3D point cloud model of the premises based on 3D data collected by the 3D scanner of the UAV, identify one or more features of the premises based on the 3D point cloud model and image data collected by the image sensor of the UAV, and generate, with the control circuit, a recommendation to the customer based on the one or more features of the premises.

Generally, customers do not have ready access to a bird's eye view of their homes, do not know what their homes look like compared to other houses in the neighborhood, and do not know what their homes look like in different seasons. It can also be difficult to measure the dimensions of external structures and distances between building and landscape elements. The methods and systems described herein may provide customers a way of obtaining an image, video, and 3D model of their home from the sky and from various elevations, distances and perspectives.

In some embodiments, an unmanned aerial vehicle (UAV), also commonly referred to as a drone, may fly over and around a customer's premises to capture a detailed 3D image of the customer's premises. In some embodiments, the UAV may also acquire soil samples, thermal data, and/or environmental data. UAVs may also be send to the premises repeatedly to acquire sensor data and/or take multiple images over the course of a day as sunlight changes and/or over the course of a year as the season changes. Images captured by UAVs may be used for multiple purposes such as in a landscape design software application for planning a garden using 3D modeling. For many applications described herein, satellite images alone may not be current enough and/or detail enough. The system described herein may allow for detailed planning of exterior enhancements, decorating, photo albums, 3D printing, virtual reality, and home holography.

Customers may dispatch a UAV to their homes via a kiosk, a smart device, and/or in a retail store through customer service terminals and/or agents. The system may verify the customer's address via scanning the customer's driver's license and/or electric bill, or through the internet using the postal system. Once customer's address is confirmed, the system may send out a UAV to fly over and around a customer's property to capture a detailed 3D image. The UAV may be dispatched from either a truck or a building. The UAV may use a built-in GPS to route the path to the customer's home. The UAV may include sensors to avoid objects and fly at a set distance (e.g. 200 to 300 feet) above the houses based on a built-in altimeter. Additionally, the UAV may use laser distance sensors to travel in a straight path and avoid objects. A central computer communicating with the UAV may assist with geolocation, traffic control, obstacle identification/avoidance, and/or other navigation tasks. The central computer may coordinate UAVs to handle problem events such as low battery and/or UAV failure conditions and may reassign UAV resources to complete a task. The central computer may further coordinate multiple UAVs to improve efficiency, completeness, and accuracy. In some embodiments, the UAV may stay in constant cellular communication contact with the central computer and transmit video data when it is in the customer premises. In some embodiments, the UAVs may be configured to land and acquire soil samples as instructed. In some embodiments, one or more UAVs may take multiple images over the course of a day as the lighting conditions change. The UAV may also take images over the course of a year as the season changes. The system may gather the images take over time captured and convert the images into a 3D model for the different times of the day and times of the year. In some embodiments, a UAV may also capture/measure moisture, noise, and the thermal characteristics associated with home insulation, color and material, etc. The captured information may also be used to detect other conditions such as objects on the customer's roof, the amount of snow/ice accumulation, and damages to shingles.

In some embodiments, once a UAV survey is completed, completed 3D images of the customer premises may be made available online for the customer. A customer may use the 3D model data to 3D print a model of their house. The captured and simulated images may also be used for real estate listings and advertisements. In some embodiments, the 3D model may be used to generate a virtual reality interface that allows the users to walk through and/or around the property. In some embodiments, images of scenic views from the perspective of the house (e.g. the view of the lake from the house) may also be captured by the surveying UAVs and included in the 3D model data.

The present disclosure generally provides an automation in the surveying of a customer premises. The system may automatically control the dispatching of UAVs, and the data captured by UAVs may be used to build a 3D models of the customer premises for various applications.

In some embodiments, UAVs may be deployed to measure dimensions of and distances between structures, landscape features, plants, or other objects. Conventionally, such detailed measurements may require many survey team man hours. The disclosed system may save customers cost/time through use of one or more UAVs and/or ground robotic units to automate detailed 3D scans and other measurements of a customer premises. In some embodiments, multiple 3D scans may be stitched together to form a highly detailed model of a home, yard, and/or business property. In some embodiments, measurements may be taken from the 3D model on an as needed basis. In some embodiments, the system may concurrently gather video and data from multiple sensors allowing observation of change, rates, usage, and activity over time.

Figure 1:
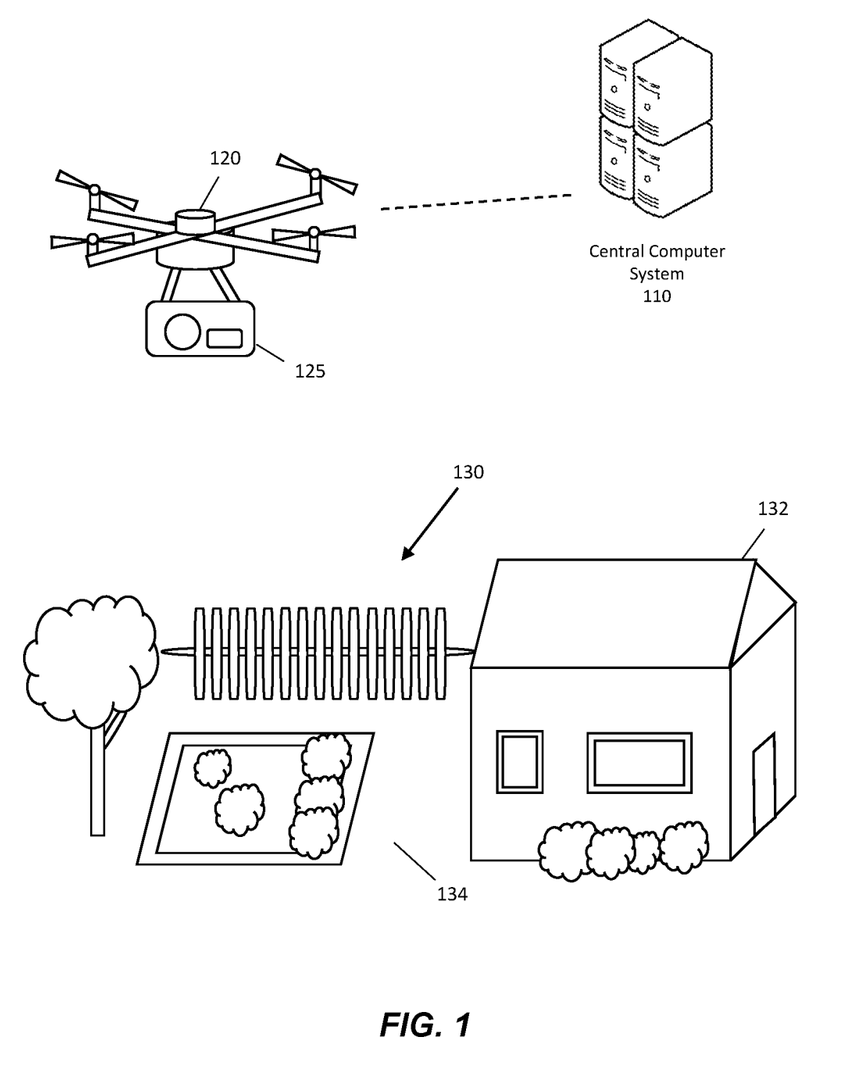
FIG. 1 is a system diagram of an overall system in accordance with several embodiments.

Referring now to FIG. 1, a system for surveying customer premises is shown. The system includes a central computer system 110 configured to communicate with a UAV 120 including a sensor device 125 to obtain data from a customer premises 130 which may include one or more structures 132 and open areas 134. The central computer system 110 may comprise a control circuit, a central processing unit, a processor, a microprocessor and the like and may be one or more of a server, a central computing system, a retail computer system, a personal computer system and the like. Generally, the central computer system 110 may be any processor-based device configured to communicate with UAVs and process image data. The central computer system 110 may include a processor configured to execute computer readable instructions stored on a computer readable storage memory, The central computer system 110 may generally be configured to cause the UAV 120 to travel to the customer premises 130 to gather a set of data and obtain a 3D model of the customer premises. Generally, central computer system 110 may perform one or more steps in the methods and processes described with reference to FIGS. 2 and 4 herein. Further details of a central computer system 110 according to some embodiment is provided with reference to FIG. 3 herein.

The UAV 120 may generally comprise an unmanned aerial vehicle configured to carry a sensor device 125 in flight and fly near the customer premises 130 for data capture. In some embodiments, the UAV 120 may comprise a multicopter configured to hover at and/or near the customer premises 130. In some embodiments, the UAV may be a quadcopter, or hexacopter, octocopter, etc. In some embodiments, the UAV 120 may comprise a communication device configured to communicate with the central computer system 110 before and/or during flight, a GPS receiver configured to provide geolocation information of the UAV 120, and a control circuit configured to control the motors driving a plurality of propellers to navigate the UAV 120. In some embodiments, the UAV 120 may include other flight sensors such as optical sensors and radars for detecting obstacles in the path of flight to avoid collisions. While only one UAV 120 is shown, in some embodiments, the central computer system 110 may communicate with and/or provide instructions to a plurality of UAVs. In some embodiments, two or more UAVs may be deployed to survey a customer premises 130 at the same time.

The sensor device 125 may comprise one or more sensors for capturing data at the customer premises 130. The sensor device 125 may comprise one or more of a 3D scanner, an image sensor, a sound sensor, a temperature sensor, a light sensor, a humidity sensor, a soil sampler, etc. In some embodiments, one or more sensors may be coupled to an actuator that pivots and/or turns the sensor relative to the body of the UAV 120. The sensor device 125 may be one or more devices attached to the UAV's body through one or more attachment means and/or may be integrated with the body of the UAV 120. While the sensor device 125 unit is shown to be attached to the bottom of the UAV 120 in FIG. 1, in some embodiments, multiple sensors may be attached to different portions of the UAV (e.g. top, wing, landing gear, etc.). In some embodiments, the sensor device 125 may be a standalone device for recording data that may operate independently when detached from the UAV 120. In some embodiments, the sensor device 125 may be at least partially integrated with the controls of the UAV 120. In some embodiments, the sensor device 125 and the UAV may share the same one or more of: a control circuit, a memory storage device, and a communication device. In some embodiments, the sensor device 125 may be communicatively coupled to the control circuit of the UAV 120 and configured to receive commands from the control circuit of the UAV 120 (e.g. began captured, end captured, rotate, etc.). In some embodiments, the sensor device 125 may comprise a communication device for independently communicating with the central computer system 110. Herein, an UAV may refer to an UAV 120 with or without a sensor device 125 attached and/or integrated with the UAV. Further details of a UAV 120 according to some embodiments is provided with reference to FIG. 3 herein.

The customer premises 130 may generally be any premises associated with a customer. In some embodiments, the customer premises may be real-estate owned, rented, and/or managed by a customer. While single residence residential premises is shown in FIG. 1, in some embodiments, the customer premises may correspond to one or more of a multi-residence residential premises (e.g. condos, apartments, duplexes, multiplexes) and non-residential premises (e.g. office building, retail building, farm, ranch, etc.). The customer premises 130 may include one or more structures 132 such as a house, a shed, a garage, a car port, a patio, a gazebo, etc. that may be scanned from the exterior of the structures. The customer premises 130 may further include one or more open areas 134 such as one or more of a front yard, back yard, side yard, etc. The UAV 120 may capture data from both structures and open areas at the customer premises and relay the captured data back to the central computer system 110. In some embodiments, the captured data may be transmitted as soon as they are captured. In some embodiments, the UAV 120 and/or the sensor device 125 may locally store at least a portion of the captured data and transfer the data to the central computer system 110 when the UAV 120 returns to a facility with recognized wireless and/or wired connection.

Figure 2:
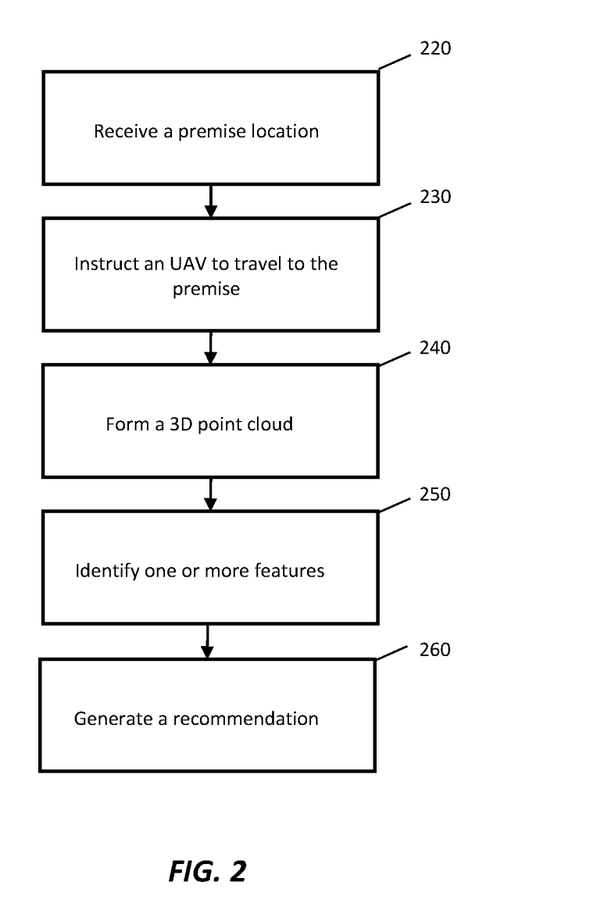
FIG. 2 is a flow diagram of a method in accordance with several embodiments.

Referring now to FIG. 2, a method of surveying customer premises is shown. In some embodiments, the steps shown in FIG. 2 may be performed by a processor-based device, such as the central computer system 110 shown in FIG. 1, the control circuit 314, and/or the control circuit 321 described with reference to FIG. 3 below. In some embodiments, the steps may be performed by one or more of a processor at the central computer system, a processor of a UAV, and a processor of a sensor device attached to the UAV.

In step 220, the system receives a premises location from a customer. The premises location may be received via a user interface device such as an in-store customer kiosk, a web-accessible user interface, a customer service counter, a mobile application, and a store customer service associate terminal, etc. The premises location information may be entered by the customer and/or an associate of a retail store. The premises location may comprise an address and/or a coordinate. In some embodiments, the user interface may display a map, a satellite view, and/or a street view to the customer to confirm the location of the premises. In some embodiments, the systems may further be configured to verify that the customer has the authority to a survey of the customer premises. For example, a user interface device and/or a store associate may verify that the entered premises information corresponds to a property owned, rented, and/or managed by the customer by scanning one or more of the customer's government issued identification (e.g. driver's license, passport, etc.), the customer's bank card (e.g. credit card, debit card, etc.), the customer's utility bills, etc. In some embodiments, the system may also display configurable access permissions to the customer in step 220 and receive the customer's selection of permissions. For example, the system may display one or more areas to survey (e.g. front yard, back yard, house, detached garage, store shed, etc.), one or more types of data to gather (e.g. 3D model, colored images, thermal images, soil sample, etc.), and one or more capture time frames (e.g. 2 pm-5 pm, weekdays only, etc.) for customer selection. In some embodiments, the system may also obtain permission to deploy stationary sensors at the customer premises via the user interface. In some embodiments, some data types and/or areas may be mandatory for enrolling into the program. In some embodiments, the customer may selectively authorize the collection of one or more types of data from one or more areas. In some embodiments, the customer may further authorize and configure repeated periodic data capture (e.g. weekly, monthly, etc.) in step 220.

In step 230, the system instructs a UAV to travel to the premises location to collect a set of data. In some embodiments, the system may determine a GPS coordinate of the customer premises based on the premises location information revised in step 220. In some embodiments, the system may use satellite image information to determine a boundary of the customer premises prior to or during step 230. In some embodiments, a central computer may further determine a route for the UAV to travel from a dispatch location to the customer premises and communicate the route to the UAV. In some embodiments, the central computer may maintain communication with the UAV to assist in the navigation as the UAV travels to the customer premises. In some embodiments, the system further determines a set of data to collect based on the information received in step 220 and communicates information relating to data to be collected to the UAV. In some embodiments, the system may select a UAV from a plurality of UAVs based on or more of customer premises location, UAV location, premises type (e.g. single residence residential premises, commercial premises, etc.), and data set to gather (e.g. UAV with required sensor types).

In some embodiments, the central computer system may maintain communication with the UAV as the UAV collects data at the customer premises. In some embodiments, the central computer may instruct the UAV to activate one or more sensors such as one or more of a 3D scanner, an image sensor, a sound sensor, a temperature sensor, a light sensor, a humidity sensor, a soil sampler, etc. at different locations and/or different orientations at the customer premises. In some embodiments, the UAV may be preloaded with a set of instructions for gathering data and be configured determine where and how to collect at least some data in the data set at the customer premises. In some embodiments, the UAV may hover at one or more locations such that the 3D scanner on the UAV may obtain scans from different angels. In some embodiments, the system may use data captured by the UAV to determine additional data to collect. For example, the system may determine additional capture locations based on the data already collected to obtain a complete data set. For example, the system may determine additional locations and/or angles to capture the data points needed to form a complete 3D model of a structure. In some embodiments, the central computer may instruct the UAV to land to collect one or more types of data in the data set. For example, a UAV may land at the customer premises prior to beginning a 3D scan. In another example, the UAV may land near or in a garden plot to sample soil with a soil sampler. In some embodiments, the system may also be configured to determine areas and/or directions to avoid. For example, the UAV may be instructed to prevent sensors from gathering data from specified areas and/or directions such that no data from neighboring premises are collected. In some embodiments, the system may be configured to automatically purge data collected from neighboring premises. For example, the system may determine a boundary of the customer premises, and avoid collecting data from structures outside of the customer premises.

In step 240, the system forms a 3D point cloud model of the premises based on the 3D data collected by the 3D scanner of the UAV. In some embodiments, the 3D scanner on the UAV may comprise a large volume 3D laser scanner such as a Faro Focus3D scanner. In some embodiments, the scanner may be configured to measure distances between the scanner and a plurality of points in its surrounding area to obtain a 3D point cloud of its surrounding. The 3D scanner may include an actuator for pointing the laser at different angles around the scanner. In some embodiments, the distance measurement may be obtained from repeated measurements of reflected laser at different angles. In some embodiments, the system and/or the 3D scanner may stitch point clouds captured at different locations to form a 3D point cloud of the premises. The stitching may be based on the location of the 3D scanner at the time of the capture. In some embodiments, the location of the 3D scanner may be based on a GPS and/or cellular receiver associated with the 3D scanner. In some embodiments, the 3D point cloud model of the premises may correspond to a high precision (e.g. centimeter, millimeter, or higher resolution and accuracy) and at-scale virtual 3D model of the customer premises.

In step 250, the system identifies one or more features of the customer premises based on the 3D point cloud model and image data collected by an image sensor of the UAV. In some embodiments, the identification of the features is based on the 3D point cloud captured by a 3D scanner and the image data collected by a colored image sensor such as a camera. In some embodiments, the image data may further comprise invisible wavelength image data such as infrared and/or ultraviolet imaging. The one or more features may be identified using object recognition algorithms and may be based on one or more of the object's color, shape, dimension, location, temperature, and identifying marking. In some embodiments, one or more features may be identified based on an active signal transmitter and/or a passive radio frequency identity (RFID) tag. In some embodiments, the system may compare portions of the 3D model and image data with a database of known features. The database of known features may comprise characteristics of objects including one or more of color, shape, dimension, likely location, likely temperature, identifying marking, 2D image, and 3D model associated with the feature. In some embodiments, the system may be configured to identify one or more of a wall, a yard, a gate, a door, a window, a planter, a roof section, a gutter, a pillar, a beam, a fence, a furniture, a security device, vegetation, and the like. Generally, a feature may be any identifiable object and/or structural element. In some embodiments, the features may further include environmental conditions such as shadows, shades, puddles, snow accumulations, etc. In some embodiments, the system may allow for manual correction of the identified objects either by associates and/or customers associated with the surveyed premises.

In step 260, the system generates a recommendation based on the one or more features identified in step 250. In some embodiments, the recommendation may comprise one or more of a product recommendation, a home service recommendation, a home improvement project recommendation, a security improvement recommendation, a lighting recommendation, and a gardening project recommendation. In some embodiments, the system may recommend products and/or services complimentary to the exiting features. For example, if a patio is identified in step 250, the system may recommend patio furniture and/or patio related home improvement projects. In another example, if a garden is identified in step 250, the system may recommend gardening tools and products. In some embodiments, the system may detect areas of possible improvement and recommend products and/or services for the improvement. For example, the system may detect a dark corner that may be of security concern to the home owner, and recommend the installation of an additional outdoor light at the location. In another example, the system may detect a broken roof tile and recommend products for repairing and/or replacing the broken tile.

In some embodiments, the system may measure a dimension of the one or more features of the premises based on the 3D point cloud model, and the customer recommendation may be based on the dimensions of the one or more features. For example, the system may measure the dimension of one or more windows from the exterior of the house and determine what blinds, shades, curtains, curtain rods, panel, etc. would fit the customer's window(s). In some embodiments, the measured dimension may be used to make custom sized window treatment for the customer. In another example, the system may measure the size of the patio and recommend patio furniture that would be suitable for the dimension of the patio. In yet another example, the system may measure the size of a garden or lawn and recommend an amount of seed, turf, and/or fertilizer to purchase. In yet another example, the system may measure the width of a side yard and recommend shed, air conditioning unit, etc. that would fit in the side yard. In still another example, the system may measure the size of light bulbs, gutters, tiles, beams, etc. and recommend replacement parts of the same sizes. In some embodiments, the 3D point cloud allows for high precision measurements to be carried out. For example, the system may be able to measure the dimension of a feature down to within centimeter or millimeter of accuracy.

In some embodiments, the recommendation may further be based on other types of data gather by the UAV and/or other sensors at the customer premises. In some embodiments, the UAV may further comprise one or more of sensors for temperature measurements, lighting condition measurements, and humidity measurements. A thermal imagining sensor may be used to detect any insulation issues at the customer premises, and the system may recommend temperature insulation products if problems are detected. In some embodiments, the temperature insulation products may be recommended based on the window and/or door sizes measured from the 3D point cloud model. In some embodiments, the UAV further comprises a soil sampler for collecting and/or analyzing the soil quality at one or more locations at the customer premises. In some embodiments, the customer premises may have one or more of: a light sensor, rain sensor, humidity sensor, a wind sensor, a temperature sensor, and a motion sensor. The on-premises sensors may provide data to the central computer via the UAV and/or via a separate network connection. The soil sample information and the on-premises sensors may provide additional information to system to generate the recommendation.

In some embodiments, the recommendation may be based on data captured by UAVs and/or on-premises sensors over a period of time (e.g. a day, a month, a season, a year, etc.). The captured information may be combined to determine changing conditions such as lighting conditions, rainfall, moisture, and temperature at different areas of the premises during different times of day and/or different time of the year, etc. In some embodiments, data captured over time may form a time-lapse 3D model of the customer premises that simulates the lighting conditions and/or other weather conditions at the customer premises during different times of day and of the year. In some embodiments, the system may recommend one of more plants and/or gardening tools for the customer premises based on one or more of lighting conditions, rainfall, moisture, and temperature over time at the customer premises. For example, some plants may be better suited in high moisture and low light conditions while other plants may need more sunlight exposure. In some embodiments, the system may further recommend a location at the customer's premises for planting one or more of the recommended plants based on the lighting condition in different locations. In some embodiments, the recommendation may further be based on soil sample(s) collected at the customer premises. For example, some plants may be better suited for soil types that retain more moisture while others may be better suited for soil with high sand and/or clay content. The collected soil sample may further be analyzed to provide recommendations for fertilization and/or watering schedule adjustments (e.g. use this type of fertilizer, water once a week, etc.). Generally, in some embodiments, the system may recommend products and services based on lighting, weather, climate, and soil information of the customer premises collected over a time period.

In some embodiments, the generated recommendation may be displayed to the customer via a user interface such as a kiosk, a website, and/or a mobile application. The recommendation may include options to purchase one or more recommended products and/or services. In some embodiments, the customer may access the 3D point cloud model formed in step 240 on the user interface and download and/or printout 2D and/or 3D representations of the customer premises. In some embodiments, an in-store 3D printer may be connected to a user interface for printing a 3D physical model based on the 3D point cloud model. In some embodiments, the customer may navigate a 3D simulation of the customer premises via the user interface.

Figure 3:
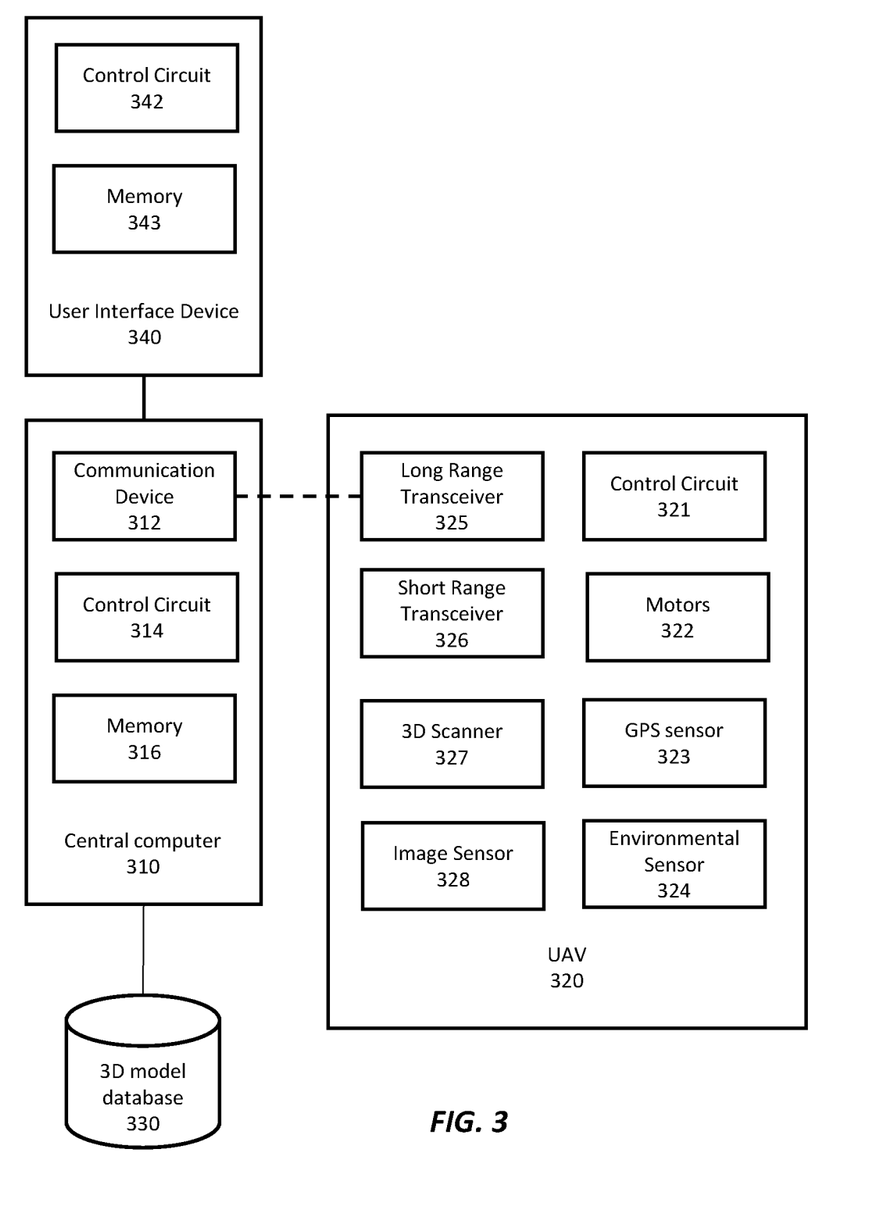
FIG. 3 is a block diagram of a system in accordance with several embodiments.

Referring now to FIG. 3, a block diagram of a system for surveying a customer premises is shown. The system includes a central computer 310, a UAV 320, a 3D model database 330, and a user interface device 340.

The user interface device 340 comprises a control circuit 342 and a memory 343. The user interface device 340 may be one or more of a kiosk, an in-store terminal, a personal computer accessing a website, a mobile device running a mobile application, etc. The control circuit 342 may be configured to execute computer readable instructions stored on a memory 343. The computer readable storage memory 343 may comprise volatile and/or non-volatile memory and have stored upon it a set of computer readable instructions which, when executed by the control circuit 342, causes the control circuit 342 to provide an user interface to a customer and exchange information with the central computer 310 via the user interface. The user interface device 340 may further comprise one or more user input/output devices such as a touch screen, a display, a keyboard, etc. that allows a user to enter premises location and/or authentication information. The user interface device 340 may further allow the user to receive and view recommendations generated by the central computer 310 and/or retrieve a 3D model of the customer premises. In some embodiments, the user interface device 340 may be owned and/or operated by a customer and/or a retail store. The user interface device 340 may further include a network interface for communicating with the central computer 310 via a network such as the Internet and/or a store's private network. In some embodiments, the user interface device 340 may further include a scanner and/or an reader for scanning an image, an optical code, a magnetic trip, an integrated circuit (IC) chip, and/or a RFID tag on one or more of the customer's government issued identification (e.g. driver's license, passport, etc.), the customer's bank card (e.g. credit card, debit card, etc.), and the customer's utility bills for identity verification.

The central computer 310 comprises a communication device 312, a control circuit 314, and a memory 316. The central computer 310 may be one or more of a server, a central computing system, a retail computer system, and the like. In some embodiments, the central computer 310 may be the central computer system 110 in FIG. 1. In some embodiments, the central computer 310 may comprise a system of two or more processor-based devices. The control circuit 314 may comprise a processor, a microprocessor, and the like and may be configured to execute computer readable instructions stored on a computer readable storage memory 316, The computer readable storage memory 316 may comprise volatile and/or non-volatile memory and have stored upon it a set of computer readable instructions which, when executed by the control circuit 314, causes the system to provide a user interface via the user interface device 340, instruct the UAV to travel to the customer premises 130 to gather data, and process the collected data to form a 3D model of the customer premises. Generally, the computer executable instructions may cause the control circuit 314 of the central computer 310 to perform one or more steps in the methods and processes described with reference to FIGS. 2 and 4 herein.

The central computer 310 may be coupled to a 3D model database 330 via a wired and/or wireless communication channel. In some embodiments, the 3D model database 330 may be at least partially implemented with the memory 316 of the central computer 310. The 3D model database 330 may have stored upon it a plurality of 3D models of customer premises. Each 3D model may comprise 3D point clouds of structures, objects, and/or terrain of the customer premises. In some embodiments, the 3D model may further include image sensor data such as visible and invisible wavelength images overlaid on the 3D model. In some embodiments, the 3D model may further include data collected by environmental sensors such as a light sensor, rain sensor, humidity sensor, a wind sensor, a temperature sensor, and a motion sensor. In some embodiments, a 3D model may comprise a time-lapse model formed by combining data captured at time intervals over a period of time. For example, data captured at different time of the year may be combined for form a time-lapse 3D model containing environmental change information (e.g. sunlight, sun angle, temperature, rainfall, moisture, etc.) for different time periods. The central computer 310 may be configured to update the 3D model database 330 each time a UAV 320 is sent to survey a customer premises and/or when sensor data is received from stationary sensor(s) at the customer premises. The central computer 310 may further retrieve information from the 3D model database 330 to generate a recommendation to a customer. In some embodiments, the customer may access at least some of the information stored in the 3D model database 330 via a user interface provided by the central computer 310. For example, a customer may view, download, and/or edit the 3D model of premises associate with the customer via the user interface. In some embodiments, the 3D model may be sent to a 3D printer to print a physical 3D model of the customer premises.

The UAV 320 may comprise an unmanned aerial vehicle configured to carry sensors and fly near a customer premises for data capture. In some embodiments, the UAV 320 may comprise a multicopter configured to hover at or near the customer premises. For example, the UAV may be a quadcopter, or hexacopter, octocopter, etc. In some embodiments, the UAV 320 may be the UAV 120 in FIG. 1. The UAV 320 includes a control circuit 321, motors 322, a GPS sensor 323, one or more environmental sensors 324, a long range transceiver 325, a short range transceiver 326, a 3D scanner 327, and an image sensor 328.

The control circuit 321 may comprise one or more of a processor, a microprocessor, a microcontroller, and the like. The control circuit 321 may be communicatively coupled to one or more of the motors 322, the GPS sensor 323, the one or more environmental sensors 324, the long range transceiver 325, the short range transceiver 326, the 3D scanner 327, and the image sensor 328. Generally, the control circuit 321 may be configured to navigate the UAV 320 based on instructions received form the central computer 310 and cause the sensors to gather a set of data at the customer premises. In some embodiments, the UAV 320 may include separate control circuits for controlling the navigation of the UAV 320 and operating at least some of the sensor devices carried by the UAV 320.

The motors 322 may be motors that controls one or more of a speed and/or orientation of one or more propellers on the UAV 320. The motors 322 are configured to be controlled by the control circuit 321 to lift and steer the UAV 320 in designated directions. The GPS sensor 323 may be configured to provide a GPS coordinate to the control circuit 321 for navigation. In some embodiments, the UAV 320 may further include an altimeter for providing altitude information to the control circuit 321 for navigation. Generally, the UAV may use the GPS and the altimeter readings to stay on a predetermined route to and from a customer premises.

The long range transceiver 325 may comprises one or more of a mobile data network transceiver, a satellite network transceiver, a WiMax transceiver, and the like. Generally, the long range transceiver 325 is configured to allow the control circuit 321 to communicate with the central computer 310 while the UAV 320 is in flight and/or at a customer premises. In some embodiments, the central computer 310 maintains communication with the UAV 320 as the UAV 320 travels to the customer premises and capture data.

The short range transceiver 326 may comprise one or more of a Wi-Fi transceiver, a Bluetooth transceiver, a RFID reader, and the like. Generally, the short range transceiver 326 has a range of several feet and is configured to allow the control circuit 321 to communicate with one or more sensors at the customer premises. The customer premises may include one or more stationary sensors such as a light sensor, a rain sensor, a humidity sensor, a wind sensor, a temperature sensor, and a motion sensor. In some embodiments, the on-premises sensor may be initially placed by a UAV, a service personnel, and/or a customer. The control circuit 321 may retrieve data collected by the stationary sensors via the short range transceiver 326. In some embodiments, the collected data may comprise a history of measurements taken over time. In some embodiments, the control circuit 321 may be configured to activate a stationary sensor to begin data collection via the short range transceiver 326. In some embodiments, the stationary sensors may communicate directly with the central computer 310 via the internet.

The 3D scanner 327 generally comprises a scanner configured to generate a 3D point cloud of at least part of its surroundings. The 3D scanner 327 may comprise a large volume 3D laser scanner such as a Faro Focus3D scanner. In some embodiments, the 3D scanner 327 may be configured to measure the distance between the scanner and a plurality of points in its surrounding to obtain a 3D point cloud of its surroundings. The 3D scanner 327 may include an actuator for pointing the laser at different angles around the scanner. In some embodiments, the distance measurement may be obtained from repeated measurements of reflected laser at different angles. In some embodiments, the central computer 310 and/or the 3D scanner 327 may stitch point clouds captured at different locations and/or perspectives to form a 3D point cloud of the premises.

The image sensor 328 may comprise visible and/or invisible light spectrum image sensors. In some embodiments, the image sensor 328 may comprises a 2D image sensor such as a colored image camera and/or a thermal camera. In some embodiments, the image sensor 328 may capture images from the same perspectives as the 3D scanner to correlate the distance measurements made by the 3D scanner with the image information captured by the image sensor 328.

The environmental sensor 324 may comprise one more sensors for gathering environmental data. In some embodiments, the environmental sensor 324 may comprise one or more of a temperature sensor, a light sensor, a humidity sensor, and a soil sampler. In some embodiments, a soil sampler may comprise a soil collector that is configured to collect soil from the customer premises to be analysis at a later time at a different location. In some embodiments, a soil sampler may be a probe configured to detect one or more of soil moisture, soil acidity, soil color, soil mineral content, soil density, etc., at the customer premises.

While only one UAV 320 is shown, in some embodiments, the central computer 310 may communicate with and/or control a plurality of UAVs. In some embodiments, two or more UAVs may be deployed to survey a customer premises at the same time. For example, two or more UAVs may perform 3D scans of the same premises from different angels and locations.

In some embodiments, one or more of the short range transceiver 326 and the environmental sensor may be optional to at least some UAVs in the system. In some embodiments, one or more of the 3D scanner 327, the image sensor 328, and the environmental sensor 324 may be part of a sensor device controlled by a separate control circuit. The sensor device may communicate with the control circuit 321 via a local connection and/or the central computer 310 via the long range transceiver 325 and/or a separate transceiver. In some embodiments, the data collected by one or more of the 3D scanner 327, the image sensor 328, and the environmental sensor 324 may be communicated back to the central computer 310 substantially in real-time. The central computer 310 may use the collected data to determine further instructions for the UAV 320 at the customer premises. In some embodiments, the data collected by one or more of the 3D scanner 327, the image sensor 328, and the environmental sensor 324 may be stored on a memory device on the UAV 320 and transferred to the central computer 310 at a later time.

In some embodiments, the UAV 320 may further include other flight sensors such as optical sensors and radars for detecting obstacles in the path of flight. In some embodiments, one or more of the 3D scanner 327, the image sensor 328, and the environmental sensor 324 may also be used as navigation sensors.

Figure 4:
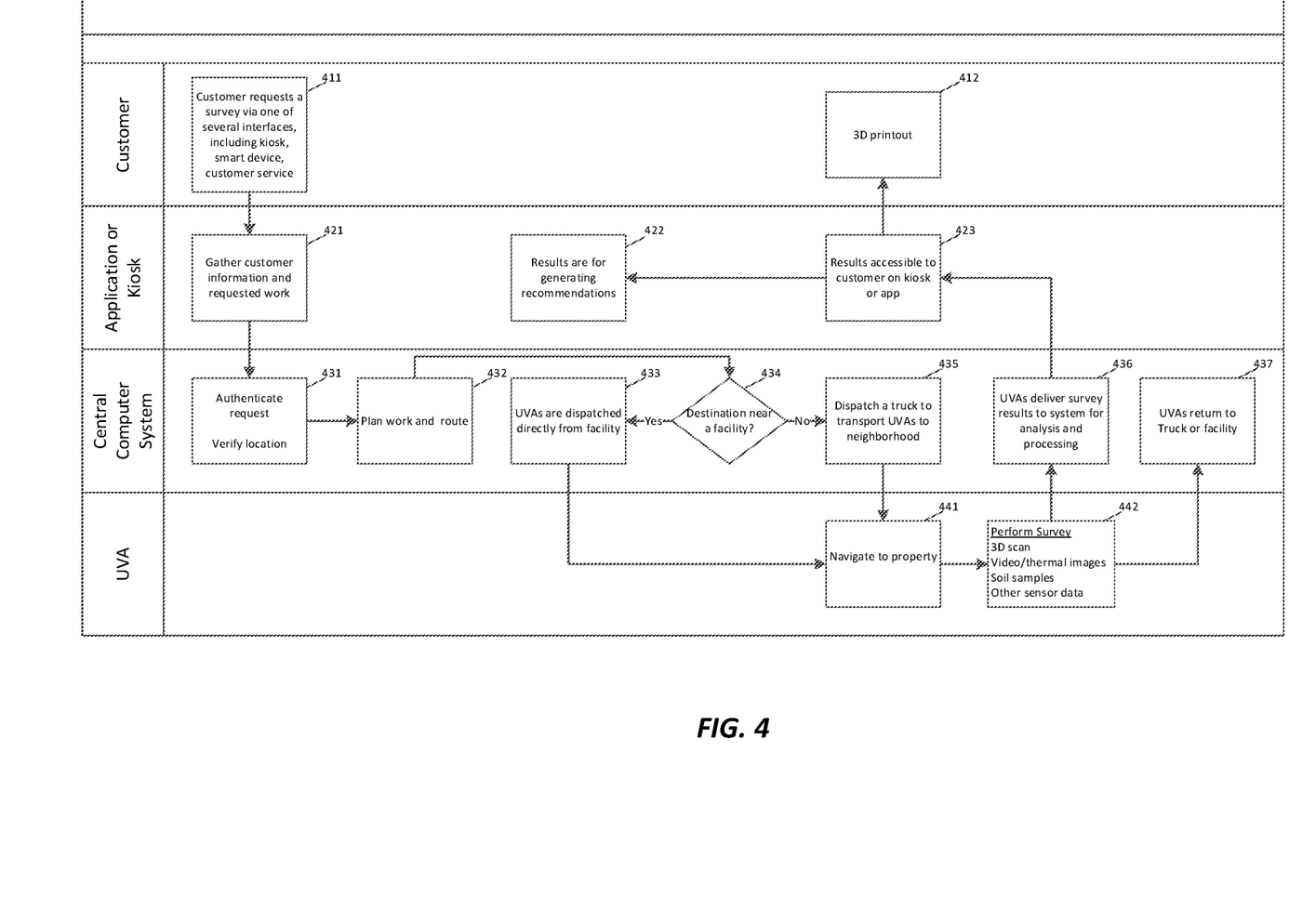
FIG. 4 is a process diagram in accordance with several embodiments.

Referring now to FIG. 4, a process for surveying a customer premises is shown. In step 411, a customer requests a survey via one or more of a kiosk, a smart device, and customer service terminal. The survey request may be submitted via a user interface. In step 421, the application or kiosk providing the user interface gathers customer information and the requested work. The requested work may specify areas to be surveyed and/or types of data to collect. In step 431, the central computer system authenticates the request and verifies the entered location. The authentication of the request may include authenticating the identity of the requester and verifying that the requester has the authority to request a survey of the entered premises.

In step 432, the central computer system plans the work and the route to be carried out by a UAV. In step 434, the central computer system determines whether the destination is near a facility housing UAVs on stand-by. If the destination is near a UAV facility, UAV(s) are dispatched directly from the facility in step 433. If the destination is not near a UAV facility, a system may also dispatch a UAV carrying truck to transport UAV(s) to the neighborhood of the destination in step 435.

In step 442, the UAV navigates to the premises of the customer. In step 442, the UAV performs the survey. The survey may include obtaining one or more of a 3D scan, colored images, videos, thermal images, soil samples, and other sensor data such as environmental measurements. At the completion of the premises survey, the central computer system navigates the UAVs back to the track or the UAV facility in step 437.

In step 436, the UAV(s) deliver survey results to the central computer system for analysis and processing. In step 436, the results of the survey are made accessible to the customer via a user interface provided by a kiosk, a website, and/or a mobile application. In step 412, the customer may elect to produce a 3D printout of the surveyed premises. In step 422, the results of the survey may be used to generate recommendations to the customer. The recommendation may comprise one or more of: a product recommendation, a home service recommendation, a home improvement project recommendation, a security improvement recommendation, a lighting recommendation and a gardening project recommendation.

In one embodiment, a system for surveying premises of a customer comprises: an unmanned aerial vehicle (UAV) comprising a three dimension (3D) scanner and an image sensor, and a control circuit comprising a communication device configured to communicate with the UAV. The control circuit being configured to: receive, from a customer, a premises location, instruct the UAV to travel to the premises location to collect a set of data, form a 3D point cloud model of the premises based on 3D data collected by the 3D scanner of the UAV, identify one or more features of the premises based on the 3D point cloud model and image data collected by the image sensor of the UAV, and generate, with the control circuit, a recommendation to the customer based on the one or more features of the premises In one embodiment, a method for surveying premises of a customer comprises: receiving, from a customer, a premises location, instructing an unmanned aerial vehicle (UAV) to travel to the premises to collect a set of data, the UAV comprises a three dimension (3D) scanner and an image sensor, forming a 3D point cloud model of the premises based on 3D data collected by the 3D scanner of the UAV, identifying one or more features of the premises based on the 3D point cloud model and image data collected by the image sensor of the UAV, and generating, with the control circuit, a recommendation to the customer based on the one or more features of the premises.

In one embodiment, an apparatus for surveying premises of a customer, comprises: a three dimension (3D) scanner configured to generate a 3D point cloud, an image sensor, an environmental sensor, a communication device configured to communicate with a server, an unamend aerial vehicle (UAV) carrying the 3D scanner, the image sensor, the environmental sensor, the communication device, and a control circuit. The control circuit being configured to: receive a premises location of the premises and a set of data to collect from the server via the communication device, cause the UAV to travel to the premises location, cause the 3D scanner, the image sensor, and the environmental sensor to collect the set of data at the premises, and transmit the set of data to the server.

Those skilled in the art will recognize that a wide variety of other modifications, alterations, and combinations can also be made with respect to the above described embodiments without departing from the scope of the invention, and that such modifications, alterations, and combinations are to be viewed as being within the ambit of the inventive concept.

What is claimed is:

1. A system for surveying premises of a customer comprising:

an unmanned aerial vehicle (UAV) comprising a three dimension (3D) scanner and an image sensor; and
    a control circuit comprising a communication device configured to communicate with the UAV, the control circuit being configured to:
    receive, from the customer, a premises location;
    instruct the UAV to travel to the premises location to collect a set of data;
    form a 3D point cloud model of the premises based on 3D data collected by the 3D scanner of the UAV;
    identify one or more features of the premises based on the 3D point cloud model and image data collected by the image sensor of the UAV;
    measure a dimension of the one or more features of the premises based on the 3D point cloud model;
    select a plurality of parts for home improvement based on sizes of the plurality of parts for home improvement and the dimension of the one or more features measured based on the 3D point cloud model; and
    generate, with the control circuit, a recommendation for the plurality of parts for home improvement to the customer.

2. The system of claim 1, wherein the premises location is received via an in-store customer kiosk.

3. The system of claim 1, wherein the set of data collected by the UAV comprises one or more of: 3D measurements, colored photographs, temperature measurements, lighting condition measurements, and humidity measurements.

4. The system of claim 1, wherein the 3D scanner comprises a laser scanner.

5. The system of claim 1, wherein the UAV further comprises a soil sampler, and the recommendation to the customer is further based on a soil sample analysis.

6. The system of claim 1, wherein the UAV further comprises a communication device for communicating with one or more stationary sensors located at the premises.

7. The system of claim 6, wherein the one or more stationary sensors comprise one or more of: a light sensor, rain sensor, humidity sensor, a wind sensor, a temperature sensor, and a motion sensor.

8. The system of claim 1, wherein the one or more features of the premises comprise one or more of a wall, a yard, a gate, a door, a window, a planter, a roof section, a gutter, a pillar, a beam, a fence, a furniture, a security device, and vegetation.

9. The system of claim 1, wherein the control circuit is further configured to generate one or more of: a product recommendation, a home service recommendation, a home improvement project recommendation, a security improvement recommendation, a lighting recommendation and a gardening project recommendation.

10. A method for surveying premises of a customer comprising:

receiving, from the customer, a premises location;
    instructing, with a control circuit, an unmanned aerial vehicle (UAV) to travel to the premises to collect a set of data, the UAV comprises a three dimension (3D) scanner and an image sensor;
    forming, with the control circuit, a 3D point cloud model of the premises based on 3D data collected by the 3D scanner of the UAV;
    identifying, with the control circuit, one or more features of the premises based on the 3D point cloud model and image data collected by the image sensor of the UAV;
    measuring a dimension of the one or more features of the premises based on the 3D point cloud model;

selecting a plurality of parts for home improvement based on sizes of the plurality of parts for improvement and the dimension of the one or more features measured based on the 3D point cloud model; and generating, with the control circuit, a recommendation for the plurality of parts for home improvement to the customer based on the one or more features of the premise.

11. The method of claim 10, wherein the premises location is received via an in-store customer kiosk configured to authenticate the customer.

12. The method of claim 10, wherein the set of data collected by the UAV comprises one or more of: 3D measurements, colored photographs, temperature measurements, lighting condition measurements, and humidity measurements.

13. The method of claim 10, wherein the 3D scanner comprises a laser scanner.

14. The method of claim 10, wherein the UAV further comprises a soil sampler, and the recommendation to the customer is further based on a soil sample analysis.

15. The method of claim 10, wherein the UAV further comprises a communication device for communicating with one or more stationary sensors located at the premises.

16. The method of claim 15, wherein the one or more stationary sensors comprise one or more of: a light sensor, rain sensor, humidity sensor, a wind sensor, a temperature sensor, and a motion sensor.

17. The method of claim 10, wherein the one or more features of the premises comprise one or more of a wall, a yard, a gate, a door, a window, a planter, a roof section, a gutter, a pillar, a beam, a fence, a furniture, a security device, and vegetation.

18. The method of claim 10, further comprising:

generating one or more of: a product recommendation, a home service recommendation, a home improvement project recommendation, a security improvement recommendation, a lighting recommendation and a gardening project recommendation.

* * * * *

UNITED STATES PATENT AND TRADEMARK OFFICE
CERTIFICATE OF CORRECTION

PATENT NO. : 10,614,503 B2
APPLICATION NO. : 15/381749
DATED : April 7, 2020
INVENTOR(S) : Donald R. High et al.

It is certified that error appears in the above-identified patent and that said Letters Patent is hereby corrected as shown below:

In the Claims

Claim 10, Column 15, Line 7-8, delete "based on the one or more features of the premise".

Signed and Sealed this
Twenty-fifth Day of August, 2020

Andrei Iancu
*Director of the United States Patent and Trademark Office*